United States Patent [19]

Frankhouser

[11] 4,327,723

[45] May 4, 1982

[54] CATHETER SHIELD

[75] Inventor: Paul L. Frankhouser, Reading, Pa.

[73] Assignee: Arrow International, Inc., Reading, Pa.

[21] Appl. No.: 149,478

[22] Filed: May 13, 1980

[51] Int. Cl.³ .................... A61M 5/00; A61M 25/00
[52] U.S. Cl. ........................ 128/214.4; 128/349 R; 128/DIG. 16; 128/DIG. 9
[58] Field of Search ............... 128/347, 350 R, 348, 128/214.4, DIG. 16, DIG. 9, 349 R; D24/54

[56] References Cited

U.S. PATENT DOCUMENTS

| | | | |
|---|---|---|---|
| 2,937,643 | 5/1960 | Elliot | 128/DIG. 16 |
| 3,335,723 | 8/1967 | Waldman, Jr. | 128/214.4 |
| 3,709,223 | 1/1973 | Mazalalad et al. | 128/214.4 |
| 3,792,703 | 2/1974 | Moorehead | 128/214.4 |
| 3,854,483 | 12/1974 | Powers | 128/349 R |
| 3,894,540 | 7/1975 | Bonner, Jr. | 128/350 R |
| 3,898,993 | 8/1975 | Taniguchi | 128/350 R |
| 4,006,743 | 2/1977 | Kowarski | 128/214.4 |
| 4,029,099 | 6/1977 | Fifield | 128/295 |
| 4,062,363 | 12/1977 | Bonner, Jr. | 128/348 |
| 4,235,232 | 11/1980 | Spaven et al. | 128/349 R |

*Primary Examiner*—Robert Peshock
*Assistant Examiner*—Michael J. Foycik
*Attorney, Agent, or Firm*—Charles H. Lindrooth

[57] ABSTRACT

Disclosed is a shield assembly for a catheter particularly useful for the protection of flow directed catheters used in the measurement of central venous pressure and pulmonary wedge pressure. The shield assembly includes front and rear hubs sized to permit movement of the catheter therethrough and a feed tube for interconnecting the front and rear hubs. A flexible sheath interconnects the two hubs. The sheath is substantially longer than the feed tube and is collapsible to permit interconnection of the hubs by the feed tube and is extendible to shield a substantial length of catheter.

9 Claims, 6 Drawing Figures

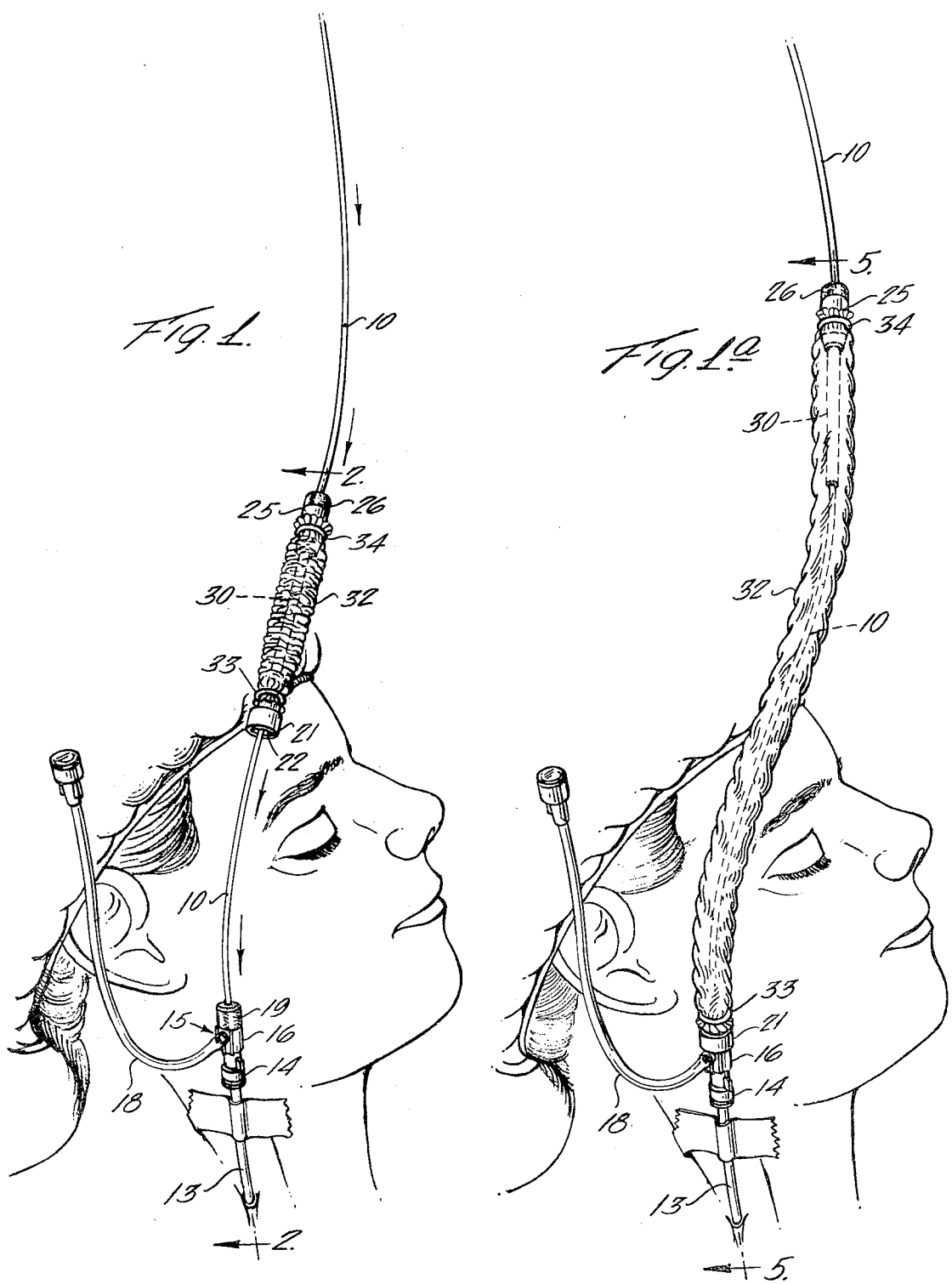

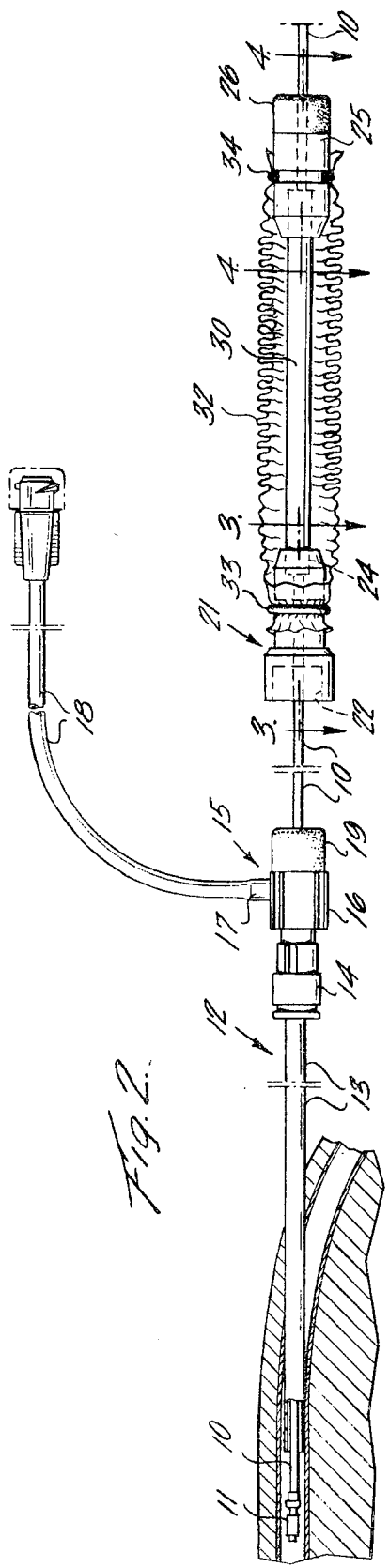
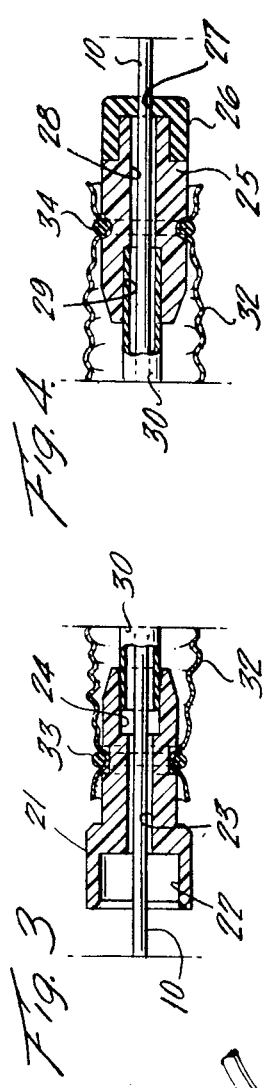
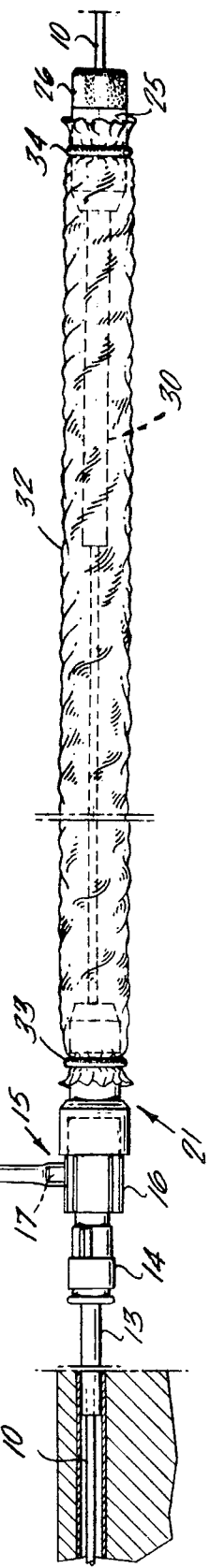

CATHETER SHIELD

FIELD OF THE INVENTION

This invention relates to apparatus for protecting a catheter from contamination during and after the time the catheter is inserted into a venous lumen or other body cavity of a human or animal.

BACKGROUND AND THE PRIOR ART

The invention is particularly useful for the protection of flow directed catheters used in the measurement of central venous pressure and pulmonary wedge pressure during and after cardio-pulmonary bypass surgical procedures.

In these procedures, the patient is monitored using a pulmonary artery balloon tipped catheter having at least two lumens. The catheter is placed percutaneously before induction of anesthesia. In certain instances it has been observed that the balloon of the catheter will fail to wedge after cardio-pulmonary bypass and the catheter has to be repositioned. Manipulation of the catheter to reposition it is recognized to be hazardous because over a period of time exposed segments of the catheter may have become contaminated and introduction of this exposed portion may cause infection.

In accordance with prior art practice for the insertion of the catheter, a vein such as the right internal jugular vein of the patient is entered with a hollow needle over which a teflon radio-opaque catheter may be placed. If the radio-opaque catheter is used the needle is removed and a stainless steel wire guide is then introduced through the catheter into the lumen of the vein. After removal of the catheter, an introducer device is passed over the guide through a small incision into the lumen of the vein. The wire guide is then removed and the flow directed catheter inserted and positioned through the introducer device. Known practice also involves the use of a plastic sheath which is tied or otherwise secured at one end to the introducer. After the catheter has been completely advanced to the wedge position, the opposite end of the sheath is fully extended over the catheter to a position remote from the introducer. This end is then fastened in place by a sterile fastening so that a length of catheter between the introducer and the opposite end of the sheath is maintained in sterile condition. This length, which may be as long as 25 in., can be advanced easily into the vein if the catheter again has to be moved to the wedge position after dislodgement or migration.

The present invention relates to improvements in method and apparatus of catheter placement and protection by providing a disconnectible guide tube means within a flexible sheath for ease of feeding a catheter through the assembly comprising the plastic sheath extending between front and rear hubs particularly when used with an adapter with side port and catheter introducer.

OBJECTS AND ADVANTAGES OF THE INVENTION

An important object of the invention is the provision for the protection from contamination of a length of an indwelling catheter thereby providing a reserve catheter portion which can be advanced into the body should the catheter require repositioning.

A further objective of the invention is the provision of simplified means providing for a sterile section of a catheter within a protective sheath which can easily and safely be advanced into the patient's body after dislodgement or migration of the catheter without fear of contamination of the patient.

A still further object of the invention is the provision of a catheter sterility shield which incorporates novel guide tube means for ease of advancement of the catheter through the protective shield when the catheter is prepared for insertion into the patient's body.

The foregoing and various other objectives which will become apparent from the following detailed description, are achieved by an assembly for an indwelling catheter comprising a rigid flanged front hub, a rear hub and an interconnecting elongated collapsible flexible sheath of transparent plastic material which is secured and sealed to the periphery of the front and rear hubs. Interconnecting the two hubs is a feed tube means preferably comprising a clear feed tube secured to one of the hubs and frictionally interconnected with the other hub. When interconnected, the length of the assembly is substantially shorter than the length of the flexible transparent plastic sheath. The rear hub is provided with an opening for advancement of a catheter through the feed tube means and through the front hub for subsequent feeding into an introducer for insertion into the patient's body. Sealing means are provided at the front and rear hubs to prevent the migration of microbiological contaminants into the shield portion of the sheath. Preferably just prior to insertion into the patient's body, while all parts are still in a sterile condition, the sheath is extended so as to provide a reserve length of catheter which is always maintained in a sterile condition.

BRIEF DESCRIPTION OF THE DRAWINGS

In the detailed description which follows, reference is made to the following figures of the drawings, illustrating a preferred embodiment of the invention:

FIG. 1 shows in diagrammatic form a catheter shield assembly with the catheter in the process of being advanced through the internal jugular vein of a human patient;

FIG. 1a is a schematic view showing the catheter after placement, with the catheter shield in the fully extended position;

FIG. 2 is a plan view, partially in section, illustrating a catheter shield assembly with parts in position corresponding to FIG. 1;

FIG. 3 is a sectional view taken along line 3—3 of FIG. 2;

FIG. 4 is a sectional view taken along line 4—4 of FIG. 2; and

FIG. 5 is a plan view, partially in section, of the catheter shield assembly with parts in position corresponding to that which is illustrated in FIG. 1a.

DETAILED DESCRIPTION OF THE DRAWINGS

Referring now to the drawings and in particular FIGS. 1 and 2, there is shown a catheter 10, which is typically of the flow directed type. As known in the art, these catheters are provided with a plurality of lumens, not shown, one of which is in communication with an inflatible balloon 11 located immediately adjacent the catheter tip. Briefly, the balloon is inflated after the catheter is placed intra thoracic and the balloon acts to gently carry the catheter through the blood stream and through the chambers of the heart into the narrowing of the pulmonary artery where it is wedged in place. The catheter is designed to monitor cardiac output in the pulmonary artery through a second lumen. Multilumen flow directed catheters capable of giving other indications of heart function have come into widespread use and give the attending physician an immediate diagnosis or indication of a patient's cardiac problems.

In accordance with preferred technique, as described above, a hollow introducer 12 comprised of an elongated tubular portion 13 and an enlarged end portion 14 having a Luer lock-type female fitting is inserted into the selected vein and taped in place.

A side port adapter assembly 15 of known construction is provided with a body portion 16 which includes a male Luer lock-type coupling for connection with the female part of the introducer 12. A side port 17 onto which is fitted a section of tubing 18 is provided for purposes to be described subsequently. Preferably, the rear end of body portion 16 is provided with a sealing member 19 having an opening extending therethrough for passage of the catheter 10 into the hollow introducer. Sealing member 19 is preferably formed of soft rubber so that that opening has good sealing characteristcs with the catheter 10. The outer periphery frictionally interfits with the front hub of the catheter shield assembly about to be described.

The catheter shield assembly includes a front hub made of a rigid sterilizable plastic material as best shown at 21 in FIG. 3, the front hub includes a flanged portion 22 which receives and sealingly interfits with the rubber hub 19. An internal passageway slightly larger in diameter than the catheter extends through the hub. The rear portion of the hub is provided with a socket 24 for purposes to be described hereinafter.

FIG. 4 illustrates the rear hub of the assembly. The rear hub comprises a body 25 on the rear end of which is fitted a sealing part 26 having opening 27 through which the catheter is passed. Part 26 is preferably formed of soft rubber or other yieldable material having good sealing characterics and yet capable of passing the balloon tip of the catheter without damage to that fragile portion. The body of rear hub 25 has an axial passage 28 extending therethrough of slightly enlarged diameter as compared with the opening in the soft rubber sealing part 26. A socket 29 is provided in the front end of the rear hub and receives a length of clear, relatively rigid tubing 30. In the preferred embodiment, the end of the tubing 30 is press fit or otherwise securred within the socket 29. The other end of tubing 30, as best illustrated in FIG. 3 is frictionally fit within the socket portion 24. The fit is such that a slight pulling pressure on the two hubs readily separates the tubing from socket 24. Tubing 30 is preferably made of a transparent plastic material such as polyvinyl chloride and provides a guide tube means for a catheter as will be described hereinafter.

Interconnecting the two hubs is a transparent sheath 32 formed of a transparent flexible material such as polyethylene or other plastic capable of preventing the passage of contaminants to the interior of the sheath. The sheath is secured and sealed to the front and rear hubs by means such as O-rings 33 and 34 through other means of sealing including ultrasonic bonding may be employed. Sheath 32 is substantially longer than the distance between the two hubs and bunches up or collapses when the inner feed tube 30 is fitted within the socket 24.

In use, the elements of the assembly described above together with the catheter and other instruments and equipment necessary for preparing the patient and positioning the introducer are supplied to the physician in sterile condition. The catheter is preassembled with the shield assembly, with the parts of the shield assembly illustrated as in FIG. 2 by advancing the catheter through the rear hub, through the guide tube means and the front hub. The catheter is advanced until the desired length indicator mark such as the 50 cm mark which is visible on its periphery, is passed out through the front hub. Where the side port assembly is used, the end of the catheter is passed through the passageway in the body of the side port assembly and advanced until about one inch extends beyond the end of the sideport assembly. The catheter can then be tested for balloon integrity. The Luer lock fittings of the introducer and the side port assembly are then interfitted and the catheter is then slowly advanced through the introducer. As soon as the tip of the catheter is intrathoracic, the balloon is inflated and the catheter is gently advanced to the wedge position. At this point there should be about 5 inches of exposed catheter between the side port assembly and the front hub. The front hub 21 is then pulled forward so that the guide tube disconnects from the front hub. The flanged socket 22 of hub 21 is advanced and fitted over sealing part 19. The protective sheath 32 then extends over the reserve length of catheter which is to be protected from contamination. Contamination is thus prevented from the introducer back to the opening 27 in the soft rubber sealing member 26. Should it become necessary to reposition the catheter, the reserve length within the protective sheath 32 is available for advancement into the patient's body without risk of contamination. The transparency of the sheath permits ready viewing of the length markings on the catheter so that the length of catheter within the patient can be readily determined. Side port 18 permits the introduction of a heparin solution through the introducer into the venous lumen and may be used for blood samplings as will be understood by those skilled in the art.

Although the invention is described for use with flow directed catheters used for the measurement of pulmonary artery wedge pressure, it should be understood that it is of use for a variety of applications wherein an indwelling catheter or catheter type device is introduced into the body wherein repositioning may be required from time to time.

I claim:

1. A shield assembly for an indwelling catheter comprising front and rear hubs each having central passages, said passages each being sized to permit movement of said catheter through said hubs, feed tube means for interconnecting said front and rear hubs including disconnectible means for separating the front hub from the rear hub, said feed tube means having a lumen extending between the passages in the hubs for the guidance of a catheter passed through the rear hub out through the front hub, a flexible sheath interconnecting the two hubs, said sheath providing a covering for the feed tube means and having a length substantially longer than the feed tube means, said sheath being collapsible to permit interconnection of the two hubs by the feed tube means for catheter guidance during feeding of a catheter through the rear hub, through the feed tube means and through the front hub and being extendible to shield a substantial length of catheter from contamination when the front hub and the rear hub are separated.

2. An assembly according to claim 1 wherein said sheath is formed of a transparent plastic material.

3. An assembly according to claim 2 wherein said feed tube means comprises a length of transparent plastic tubing.

4. An assembly according to claim 3 wherein said disconnectible means comprises a socket in said front hub coaxial with said opening on the side of the hub located interiorly of the sheath, said socket being dimensioned to receive the free end of said tube means with a friction fit between the tube and the socket permitting separation of the hubs and extension of the sheath over an elongated section of catheter.

5. An assembly for the insertion and protection of a length of an indwelling catheter from sources of contamination external of the body of the patient, said assembly comprising in combination, a catheter introducer having an elongated tube adapted to be inserted into a patient's vein for introduction of a catheter into said vein, a disconnectible fitting having a lumen therethrough and adapted to be connected to said introducer, said connection providing a seal for the lumen and the introducer against contamination by airborne contaminants, a socket at the rear end of said lumen, a catheter guide tube frictionally interfitting within said socket and extending rearwardly therefrom, a hub connected to the rear end of said guide tube, an opening in said hub, said hub opening being dimensioned to provide for passage of a catheter through the hub, through said guide tube and through said disconnectible fitting and further through the catheter introducer, a flexible sheath covering said guide tube and sealingly interconnected to said disconnectible fitting and said hub, said sheath being collapsible to permit interconnection of the hub and said disconnectible fitting for advancement of a catheter first through the rear hub, then through the guide tube and the disconnectible fitting until a length of catheter needed for introduction into the patient is advanced beyond the end of said disconnectible fitting, the sheath being extendible relative to the catheter upon advancement of the catheter into the patient to shield a substantial length of catheter beyond that advanced for introduction into the patient, the assembly comprising the introducer, the disconnectible fitting, the extended sheath and the hub all providing for isolation of the length of catheter advanced through the opening in the rear hub.

6. A method of catheterization while providing protection of a portion of the catheter not within a patient against contamination while another portion is within the patient, said method comprising providing a protective shield assembly for the catheter, said shield assembly having a front hub and a rear sealing means, and tube means releasably interconnecting said front hub and rear sealing means so as to provide a disconnectible assembly including the rear sealing means, the front hub, and the tube means, an elongated transparent plastic sheath covering said tube means and sealingly interconnecting said front hub and rear sealing means, said transparent sheath being substantially longer than said tube means, and being collapsible when the tube means interconnects the front hub and rear sealing means, said front hub and rear sealing means being adapted to receive and pass the catheter through the rear sealing means through the tube means and out through the front hub when the tube means interconnects the hub members, the steps which comprise first passing the catheter through the rear hub, the lumen of the tube means and the front hub member, and then disconnecting the front hub and rear sealing means and extending the sheath over a substantial length of the catheter by displacing the front hub member forwardly along the catheter thereby providing isolation of a substantial length of catheter from contaminants.

7. A shield assembly for an indwelling catheter advanced into the body through a tubular introducer, said assembly comprising, a front hub member, means interconnecting the hub member with the introducer, feed tube means extending rearwardly of the front hub member, a passageway through the hub member providing for the passage of a catheter advanced through the feed tube means, the front hub member and the introducer, a sheath formed of a flexible material secured to said hub and extending over the feed tube means, said sheath being substantially longer than the feed tube means, rear sealing means at the end of said sheath opposite to the hub member for sealingly connecting the sheath to the catheter, the sheath being collapsible to facilitate passage of the catheter through the rear sealing means, the feed tube means and the front hub member and thereafter being extendable relative to the catheter to shield a substantial length of catheter between the hub member and the rear sealing means and interconnecting means for interconnection of the ends of said feed tube means to the hub member and the rear sealing means during passage of the catheter through the sealing means, the feed tube means and the front hub member and including a releasable coupling to permit extension of the sheath over said substantial length of catheter after advancement of the catheter into the body.

8. A shield assembly according to claim 7 wherein the rear sealing means comprises a rear hub member having an opening sized to pass the catheter, said opening being surrounded by a resilient material which contacts the walls of the catheter, said feed tube means being secured to the rear hub member with its passage in coaxial alignment with the opening in the rear hub member, and wherein said releasable coupling is at the opposite end of said feed tube means and comprises frictionally interfitting parts on the front hub member and the feed tube means, said parts being separatable to permit extension of the sheath.

9. A shield assembly according to claim 8 wherein the sheath and the feed tube means are formed of transparent plastic materials.

* * * * *